United States Patent [19]

Burkinshaw et al.

[11] Patent Number: 6,007,537
[45] Date of Patent: Dec. 28, 1999

[54] NESTED CUTTING BLOCK

[75] Inventors: Brian D. Burkinshaw, Pflugerville; Charles W. Mumme, Austin, both of Tex.

[73] Assignee: Sulzer Orthopedics Inc., Austin, Tex.

[21] Appl. No.: 09/097,501

[22] Filed: Jun. 15, 1998

[51] Int. Cl.$^6$ ............ A61B 17/56; A61B 17/58; A61B 17/60

[52] U.S. Cl. ................................. 606/66; 606/88

[58] Field of Search ................. 606/86, 87, 88, 606/89, 96, 98, 82

[56] References Cited

U.S. PATENT DOCUMENTS

| | | | |
|---|---|---|---|
| 4,892,093 | 1/1990 | Zarnowski et al. | 606/82 |
| 5,411,505 | 5/1995 | Mumme | 606/88 |
| 5,454,816 | 10/1995 | Ashby | 606/88 |
| 5,683,397 | 11/1997 | Vendrely et al. | 606/88 |
| 5,749,876 | 5/1998 | Duvillier et al. | 606/88 |
| 5,925,049 | 7/1999 | Gustilo et al. | 606/82 |

Primary Examiner—Michael Buiz
Assistant Examiner—Vy Q. Bui
Attorney, Agent, or Firm—Philip S. Lyren; Kenneth S. Barrow

[57] ABSTRACT

A nested cutting block includes at least a first slot for guiding a saw blade during a first bone cutting operation. The first block has a cavity formed therein. A first securing interlock is formed on the first block. A second block is detachably mounted in the cavity and includes at least a second slot for guiding the saw blade during a second bone cutting operation. A second securing interlock is attached to the second block. An interlock member engages the first and second securing interlocks for detachably engaging the second block within the first block. The first bone cutting operation is made with the first and second blocks interconnected and mounted in a cutting position. The second bone cutting operation may be made with the first and second blocks nested together in the cutting position. Alternatively, the second bone cutting operation may also be made with the first block detached from the second block and the second block remaining in the cutting position.

20 Claims, 7 Drawing Sheets

6,007,537

NESTED CUTTING BLOCK

BACKGROUND

The disclosures herein relate generally to implants for prosthetic joints and more particularly to preparing cuts in bones for fitting such implants, such as preparing femoral cuts in the distal femur.

Preparing the distal femur to receive the femoral component of a knee prosthesis, involves several accurately located cuts in the bone surface of the femur. Typically, the first cut establishes a transverse surface and a second cut may establish a reference, anterior surface. This provides a locating surface for a cutting guide which is used to assist in accurately cutting the additional surfaces needed to locate and secure the implant of the femoral knee prosthesis.

One method used for preparing the additional cuts includes a combination of cutting guides commonly known as speed blocks, all-in-one blocks, and four-in-one blocks. These are cutting guides for supporting and guiding an orthopedic saw blade during the preparation of the distal femoral chamfered surfaces for the femoral component of the knee prosthesis. All chamfered and square cuts can be made with one instrument without removing the device so that the user is not forced to use an additional block or blocks with different cutting surfaces and angles to complete the cuts. Another method involves using independent chamfer blocks that only allow one, two, or more cuts. This involves removal of the first block from the bone and replacing it with a second block to complete the cuts.

One approach to this problem is disclosed in U.S. Pat. No. 4,892,093, which describes a cutting guide for guiding a saw blade during the preparation of a femur for the implant of the femoral component of the knee prosthesis. This device includes guide surfaces for enabling the cutting of the anterior femoral cut, the posterior femoral cut, the anterior chamfer cut, and the posterior chamfer cut, while the cutting guide remains located and secured to the femur in a single position on the transverse surface located along the distal femur.

Another approach is disclosed in U.S. Pat. No. 5,411,505, which describes a jig for resecting the distal end of a femur to receive the femoral component of the knee prosthesis. The jig has independent medial and lateral condyle sagittal saw guides. The guides aid the user in cutting three of four resected surfaces or planes for each condyle. The femoral component accepts shims over either condyle to compensate for uneven loss of healthy bone. Each saw guide slides on a slanted dovetail track so that the proper amount of anterior displacement can be maintained.

Presently known methods have their respective advantages and limitations. One limitation is that in one known method, the user is making blind cuts and has no accurate method for checking the flatness of each cut; a factor which can be critical for a bone-ingrowth device. Another limitation is that in another known method, the user has the advantage of being able to verify each cut with a flat, straight edge after each cut is made, for each cut surface. However, because this method requires that the blocks must be removed and replaced in the bone at least two times, error is more likely. Also, if the bone is soft, the locating holes for the blocks can become elongated, thus allowing the cutting surfaces to move when pressure from the saw blade is applied. This creates a burdensome requirement in the manufacture of these devices, because manufacturers are forced to supply both of the described types of cutting blocks on either a production and/or custom basis to satisfy customer demand.

Therefore, what is needed is a device and method which gives the user the advantages of both of the above types of chamfer blocks without the limitations of each, and which permits the manufacturers to avoid the expense of producing two different devices that perform the same function.

SUMMARY

One embodiment, accordingly, provides a device and a method which permits the user the advantage of making all sequential cuts in a total cutting operation, or making each sequential cut and progressively checking each cut separately. To this end, a nested chamfer speed block comprises a first block including a pair of first slots for guiding a saw blade during a femoral cutting operation, and having a cavity formed therein. A second block is detachably mounted in the cavity and includes a pair of second slots for guiding the saw blade during a chamfer cutting operation. Means are also provided for detachably securing the second block with the first block.

A principal advantage of this embodiment is that both the first and second blocks include saw blade guides or captures which guide the saw blade along the desired angle and trajectory, and may also allow partial exposure of the saw guide surface which the user can use as a guide for a straight edge to verify the flatness of the cut. Another advantage is that this embodiment permits the user to work quickly and accurately with the ability to visibly verify accuracy.

DETAILED DESCRIPTION OF THE PREFERRED EMBODIMENT

Figure 1:
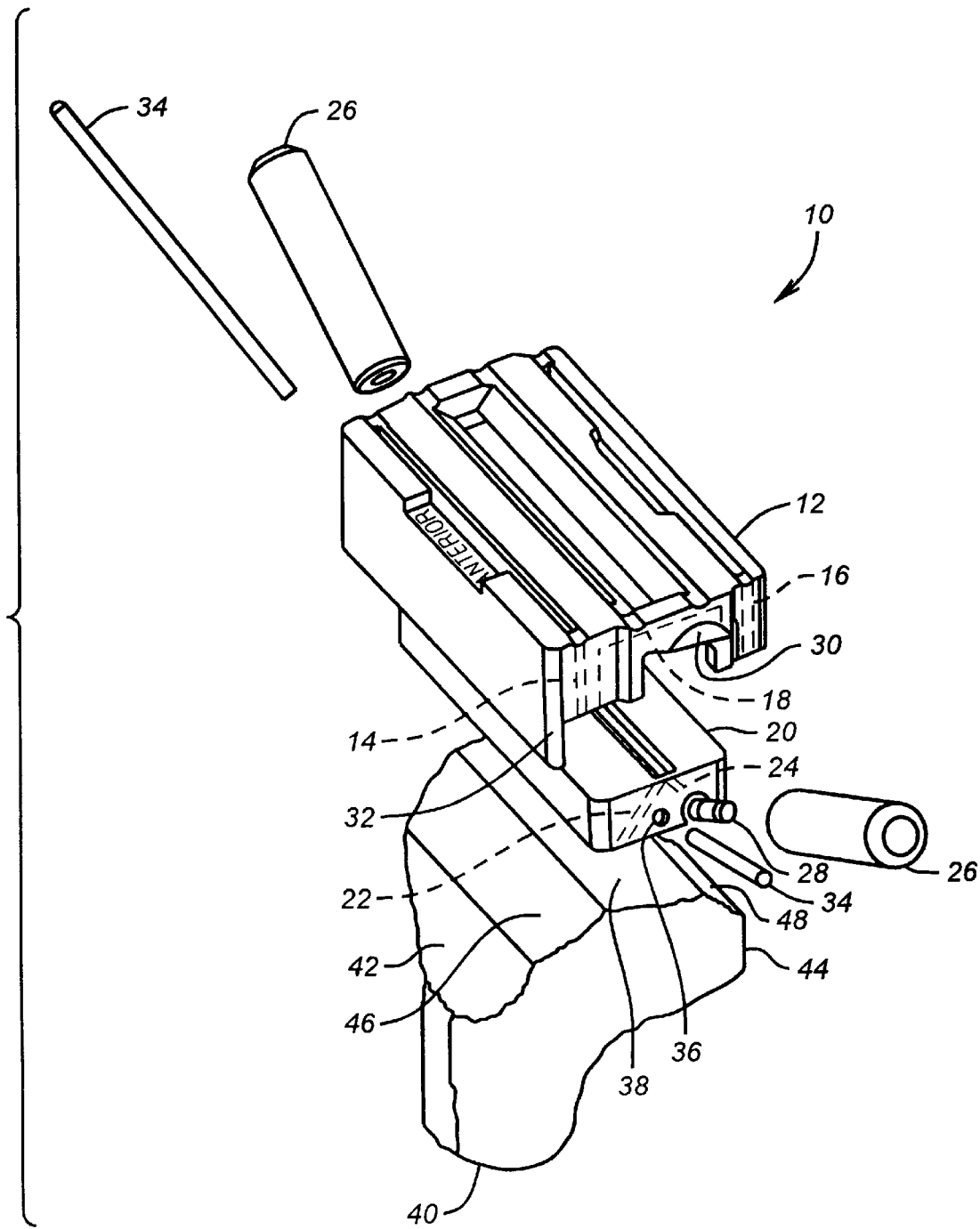
FIG. 1 is an exploded isometric view illustrating an embodiment of a pair of nested speed blocks.

In FIG. 1, a nested cutting speed block is illustrated in an exploded view and is generally designated 10. Speed block 10 includes a first block 12 including a pair of slots or saw blade guides or captures, 14 and 16 for guiding a saw blade during a femoral cutting operation. A cavity 18 is formed in first block 12. A second block 20 may be detachably mounted in the cavity 18 in a nested position and includes a pair of slots, or saw blade captures, 22 and 24 for guiding the saw blade during a chamfer cutting operation. At least one, and preferably a pair of interlocking members 26 are provided for detachably securing the second block 20 in the nested position within the first block 12. The interlocking member 26 comprises a handle and is constructed to receive and detachably secure to a securing interlock such as an attachment member 28 which extends from the second block 20. In addition, the handle 26 engages another securing interlock such as a locking recess 30 formed in the first block which permits the handle 26 to nest into the locking recess 30 and engage the first block 12.

Pins 34 are inserted into through a pair of pin holes 36 provided in second block 20, and into a transverse surface 38 formed on a distal femur 40 by a previously made, or preparatory, transverse cut. In this manner, second block 20 is secured to femur 40. As a result, when the second block 20 is secured to the distal femur 40 by pins 34 and is also nested in cavity 18, and the first block 12 and second block 20 are secured together by handles 26, which engage the attachment members 28 and locking recesses 30, the nested blocks 12 and 20 are secured as a unit to distal femur 40. Slots 14 and 16 are disposed at a first angle for the femoral cutting operation. Slots 22 and 24 are disposed at a second angle, different from the first angle, for the chamfer cutting operation. An anterior referencing member 32 may be provided to extend from the first block 12 and engage a reference surface formed on distal femur 40. In this manner, an anterior femoral surface 42 and a posterior femoral surface 44 may be formed on distal femur 40, and also an anterior chamfer surface 46 and a posterior chamfer surface 48 may be formed on distal femur 40.

Figure 2:
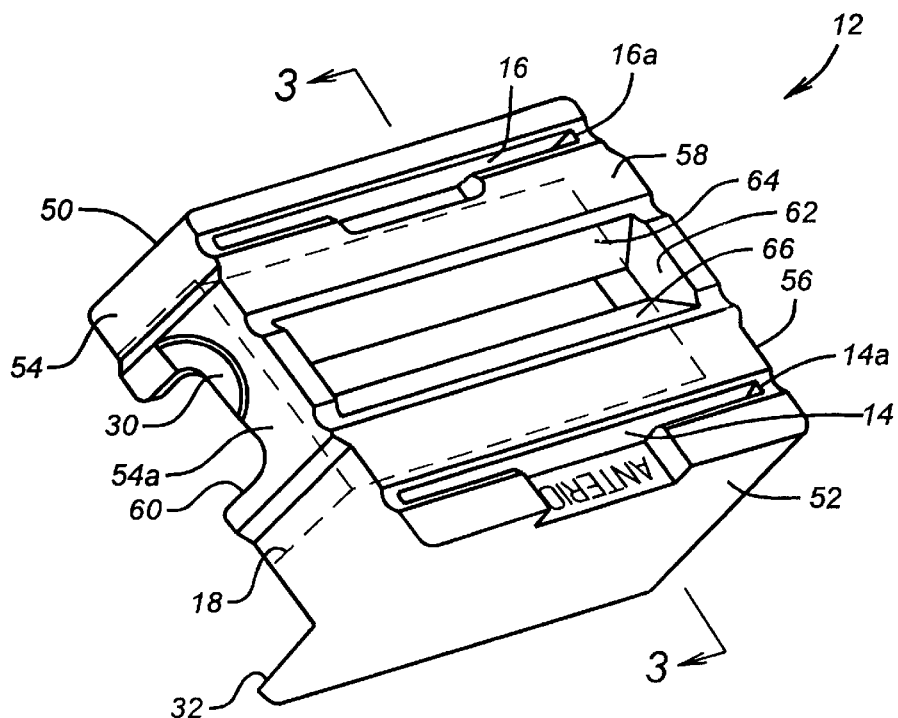
FIG. 2 is an isometric view illustrating an embodiment of a first speed block for a femoral cutting operation.

More particularly, block 12 (FIG. 2) is generally rectangular and includes opposite side walls 50 and 52, opposite end walls 54 and 56, and a top surface 58. Opposite end 54 walls and 56 are identical and therefore only end wall 54 is described in detail. An opening 60 is formed in end wall 54 which exposes a portion of second block 20 when block 20 is nested in cavity 18 of block 12. Locking recess 30 is also formed in end wall 54 and comprises a recess formed into surface 54a of end wall 54. Top surface 58 includes an opening 14a of slot 14, an opening 16a of slot 16 and a V-shaped opening 62 including a pair of opposed angled surfaces 64 and 66. Also, side wall 52 includes anterior referencing member 32 extending from side wall 52.

Figure 3:
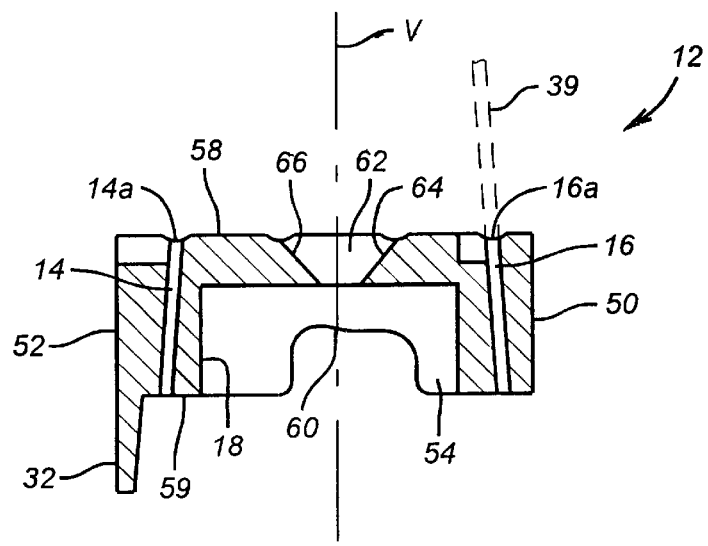
FIG. 3 is a cross-sectional view of the first block taken along line 3—3 of FIG. 2.

Again in FIG. 3 from a different perspective, block 12 includes the opposed side walls 50 and 52, and end wall 54 is visible at one end of cavity 18. Anterior referencing member extends from side wall 52. Opening 60 is formed in end wall 54. Top surface 58 includes openings 14a and 16a for slots 14 and 16 respectively, to receive a saw blade 39 for forming the femoral cuts. Angled surfaces 64 and 66 of V-shaped opening 62 are between slots 14 and 16. Also, slots 14 and 16 are at a slight angle with a vertical reference line designated V, and terminate at a bottom surface 59 of block 12.

Figure 4:
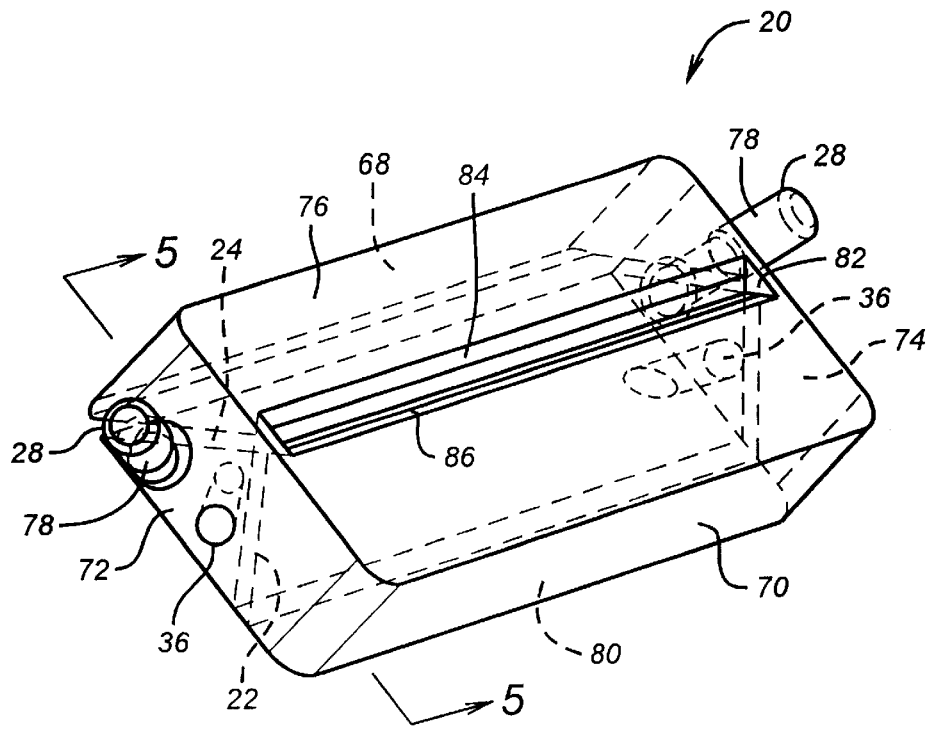
FIG. 4 is an isometric view illustrating an embodiment of a second speed block for a chamfer cutting operation.

Block 20 (FIG. 4) is generally rectangular and includes opposite sidewalls 68 and 70, opposite end walls 72 and 74, and a top surface 76. Opposite end walls 72 and 74 are identical and therefore only one end wall 72 is described in detail. End wall 72 includes attachment member 28 and pin hole 36. The attachment member is rigidly attached to and extends outwardly from end wall 72. A receiving end 78 of attachment member 28 receives handle 26, FIG. 1 and may be configured for a threaded, clamping or other appropriate connection with handle 26. Pin hole 36, FIG. 4, is angled downwardly toward and terminates at a bottom surface 80 of block 20 which seats on transverse surface 38, FIG. 1, of distal femur 40. In this manner pin 34 is driven through pin hole 36 and downwardly into distal femur 40 at transverse surface 38. When both pins 34 secure block 20 to distal femur 40, a macro lock is formed. Top surface 76, FIG. 4, of block 20 includes a V-shaped opening 82 of slots 22 and 24. Opening 82 includes a pair of opposed angled surfaces 84 and 86.

Figure 5:
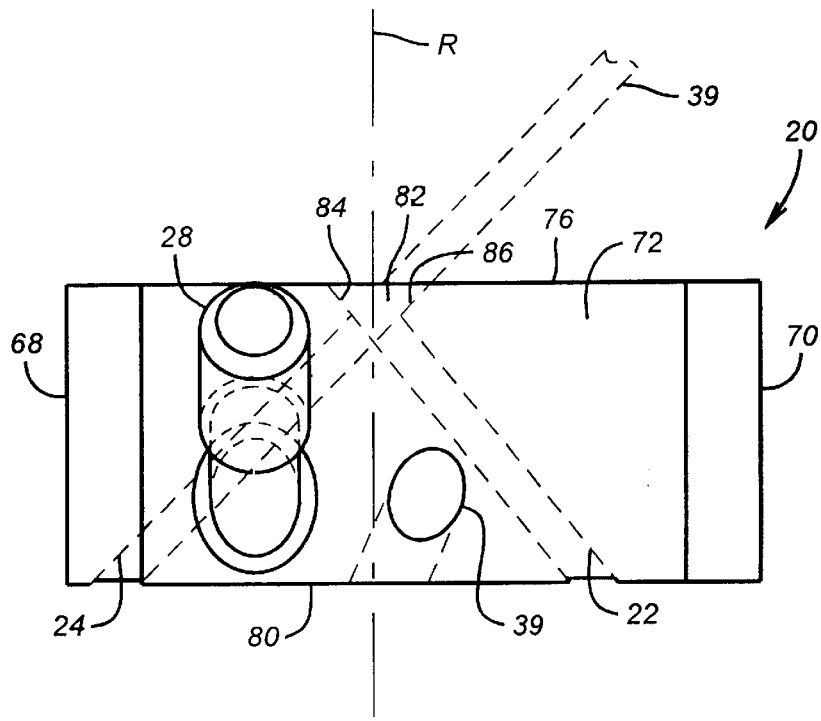
FIG. 5 is an end view of the second block taken along the line 5—5 of FIG. 4.

Again in FIG. 5, from a different perspective, block 20 includes opposed side walls 68 and 70, and end wall 72 includes attachment member 28 and pin hole 36. Top surface 76 includes V-shaped opening 82 of slots 22 and 24 including opposed angled surfaces 84 and 86, for receiving saw blade 39. Slots 22 and 24 are at an angle with a vertical reference line designated R, and terminate at bottom surface 80 of block 20. The angle of slots 22 and 24 is greater than the angle of the slots 14 and 16, FIG. 3 for forming the chamfer cuts. Also, when block 20 is nested in block 12, angled surface 84 and 86 of block 20, FIG. 5, respectively align with angled surfaces 64 and 66 of block 12, FIG. 3.

Figure 6:
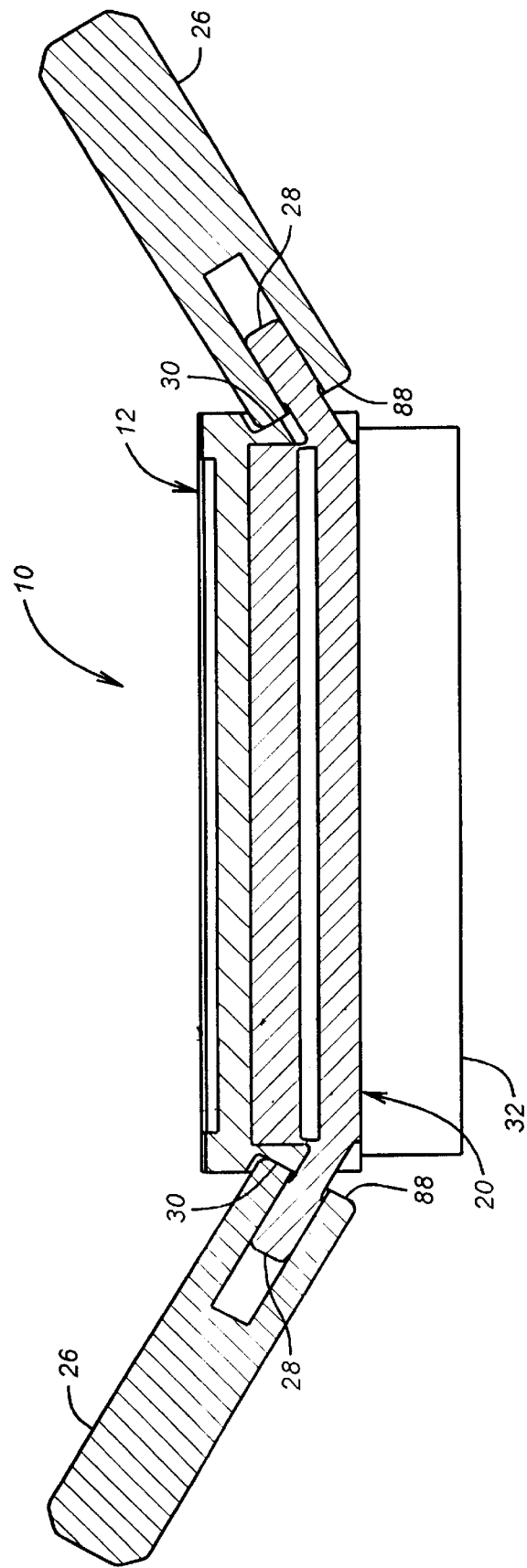
FIG. 6 is a cross-sectional frontal view illustrating an embodiment of the nested blocks.
Figure 6A:
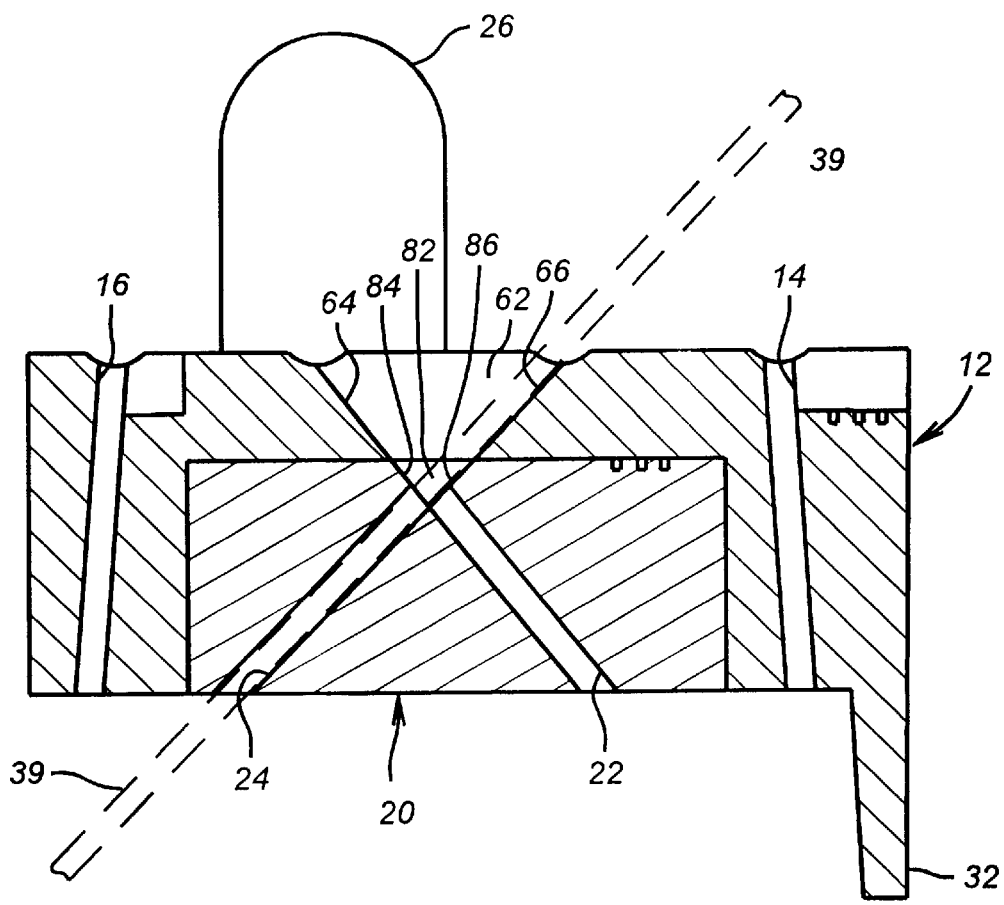
FIG. 6a is a cross-sectional side view illustrating the nested blocks of FIG. 6.

Nested blocks 12 and 20, FIG. 6 and 6a, are secured together when handles 26 are secured to their respective attachment members 28 which extend outwardly from block 20. As it can be seen, when handles 26 are fully seated on attachment member 28, an end 88 of handles 26, seats in recess 30 of block 12, thus securing blocks 12 and 20 together in a detachable manner to form speed block 10. As a result, when blocks 12 and 20 are nested, saw blade 39 can be inserted through V-shaped opening 62 of block 12 and V-shaped opening 82 of block 20. Saw blade 39 can then be inserted into slot 22 of block 20 in alignment with surfaces 64 and 84 of blocks 12 and 20, respectively. Also, saw blade 39 can be inserted into slot 24 of block 20 in alignment with surfaces 66 and 86 of blocks 12 and 20 respectively. Thus, chamfer cuts can be made with the blocks 12 and 20 nested together. Also, if preferred, handles 26 can be removed from engagement with recesses 30 and attachment members 28. Block 12 can then be removed from block 20, and the chamfer cuts can be made with only block 20 positioned on transverse surface 38.

Figure 7:
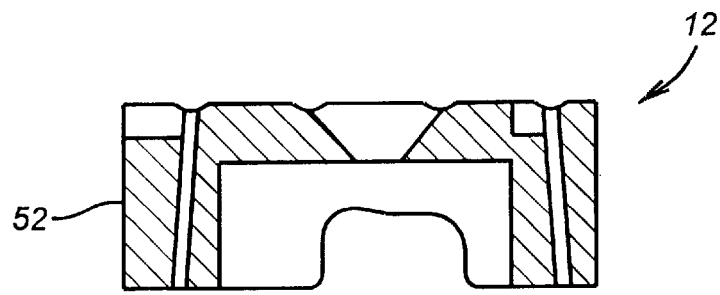
FIG. 7 is a cross-sectional view illustrating an alternative embodiment of the first block.
Figure 8:
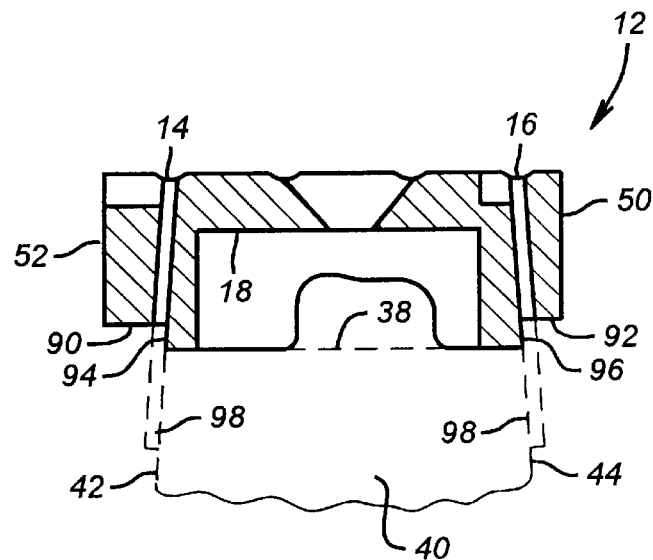
FIG. 8 is a cross-sectional view illustrating another alternative embodiment of the first block.

An alternate embodiment of block 12, FIG. 7, does not include anterior referencing member 32 extending from side wall 52 of block 12. Another alternate embodiment, FIG. 8, illustrates block 12 having cut-away portions 90 and 92 from side walls 52 and 50, respectively. The cut-away portions 90 and 92 create alignment surfaces 94 and 96, respectively, adjacent slots 14 and 16. The alignment surfaces 94 and 96 permit the user to align a straight edge 98 with the alignment surfaces 94 and 96 and with respective femoral cut surfaces 42 and 44 on distal femur 40, and make adjustments as needed. Excellent visibility of cut surfaces 100 and 44 is provided. Although not shown in FIG. 8, block 20 is nested in cavity 18 during the femoral cutting operation.

Figure 9:
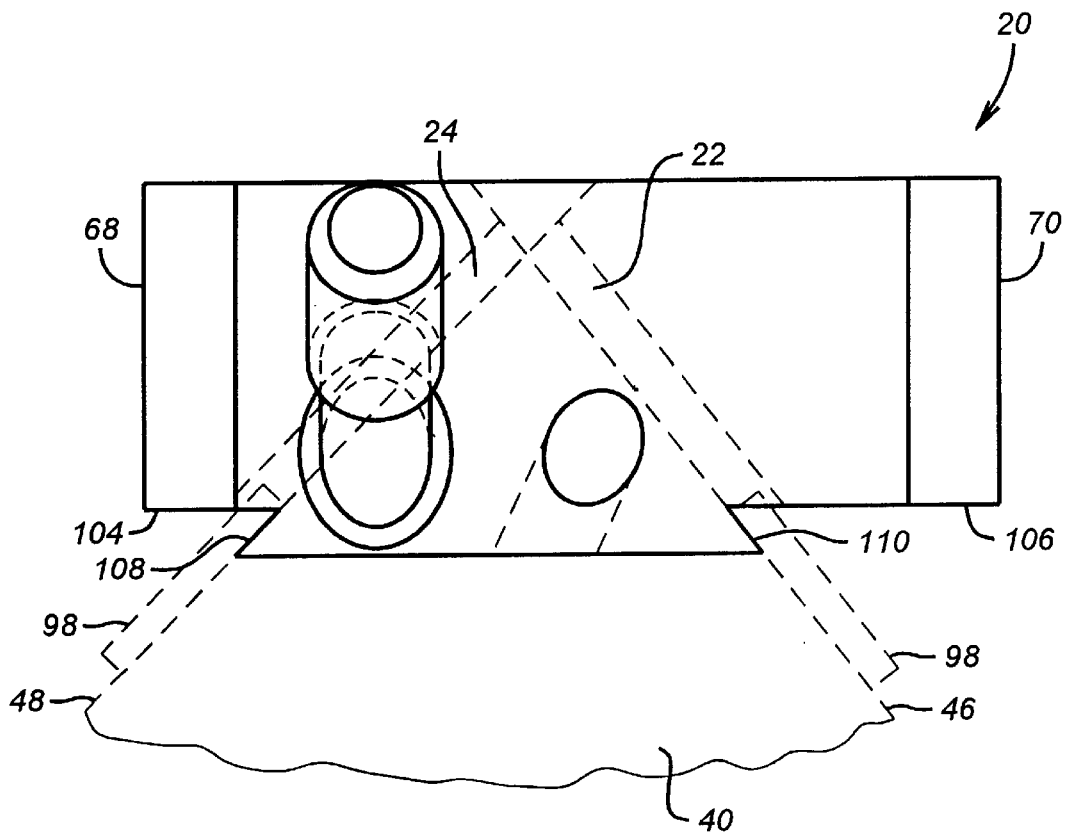
FIG. 9 is an end view illustrating an alternative embodiment of the second block.

Another alternate embodiment of block 20, FIG. 9, includes cut-away portions 104 and 106 from side walls 68 and 70 respectively. The cut-away portions 104 and 106 create alignment surfaces 108 and 110, respectively, adjacent slots 24 and 22. The alignment surfaces 108 and 110 permit the user to align the straight edge 98 with the alignment surfaces 108 and 110 and with respective chamfer cut surfaces 48 and 46 on distal femur 40, and make adjustments as needed. Excellent visibility of the cut surfaces 48 and 46 is provided because block 12 may be removed from block 20 for the chamfer cutting operation.

Figure 10:
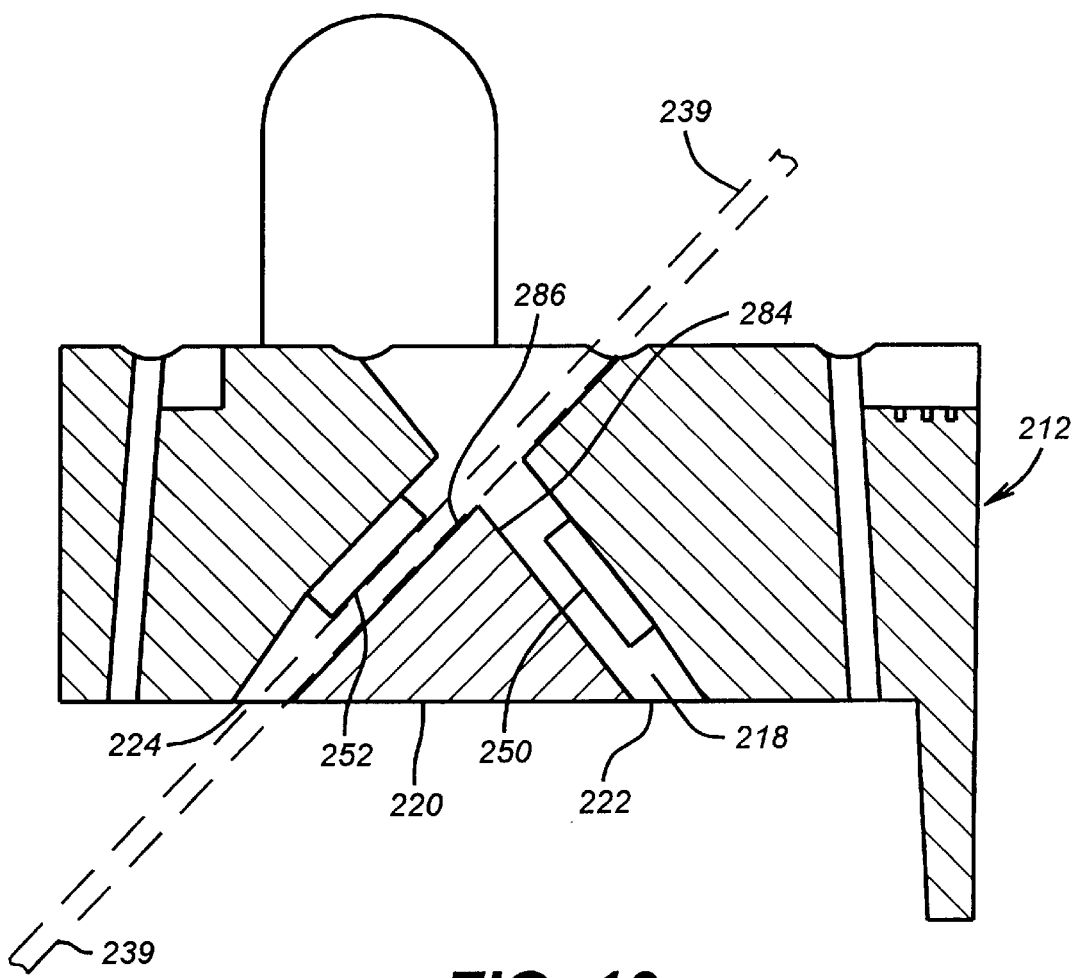
FIG. 10 is a cross-sectional side view illustrating an alternate embodiment of nested blocks.

A further alternate embodiment, FIG. 10, illustrates that block 212 may include a cavity 218 which is triangular in cross-section. Also, block 220 is triangular in cross-section rather than the rectangular cross-section of block 20, FIG. 4. As a result, slots 222 and 224, FIG. 10, are formed when block 220 is nested in cavity 218 of block 212. However, when block 212 is removed, a pair of angular surfaces 284 and 286 are exposed as cutting guides for a saw blade 239 to make chamfer cuts. Therefore, saw captures 250 and 252 are provided to extend from end-to-end along angular surfaces 284 and 286, respectively, to maintain saw blade 239 aligned with the angular surfaces 284 and 286. Saw captures 250 and 252 are attached at their respective opposite ends, to block 220, however this attachment is not visible in the cross-sectional view of FIG. 10.

In operation, the distal femur is prepared by first making a transverse cut along the top surface. A first anterior referencing cut may also be made. The second block is nested in the cavity of the first block and secured therein by the handles engaging the attachment members and engaging the locking recesses. The nested blocks are mounted on the transverse cut surface and the anterior referencing member is abutted to the anterior referencing cut. The pins are driven through the angled pin holes in opposite sides of the second block to secure the nested blocks in a macro lock on the femur. The saw blade makes the anterior and posterior femoral cuts by orientation through the angled slots in the first block. If desired, the handles may be removed from the attachment members which enables the first block to be removed from the second block. However, it is not necessary to remove the first block to permit the chamfer cuts to be made. If it is decided to remove the first block, the second block remains secured to the transverse surface of the femur by the pins. The saw blade then makes the anterior and posterior chamfer cuts by orientation through the angled slots in the second block. The pins are then removed from the femur and from the second block so that the second block may be removed from the transverse surface of the femur.

As it can be seen, the principal advantages of these embodiments are that a surgeon has an option of choosing the best method, i.e. using the nested speed blocks or another device based on personal preference, the patient's bone condition, etc. The nested speed blocks offer the advantage of speed and accuracy when used as an assembled unit. In addition, visibility of the cut surfaces during the cutting operation is available as well as the ability to physically verify cutting accuracy, flatness of the cut surface, and bone condition after each individual cut. Bone quality is better preserved because the surgeon does not have to repeatedly exchange various cut blocks which can cause damage to previously prepared bone surfaces. The accuracy factor reduces the possibility of inducing errors into the cuts because the blocks never leave the bone until after the respective cuts are completed. Inventory requirements are reduced for the manufacturer of the blocks and the customer, e.g. hospital or distributor, because the nested block device replaces the use of either the single device or the two separate devices that were previously required.

As a result, one embodiment provides a nested chamfer speed block including a first block having a pair of first slots for guiding a saw blade during a femoral cutting operation. A cavity is formed in the first block. A second block is detachably mounted in the cavity and includes a pair of second slots for guiding the saw blade during a chamfer cutting operation. An interlocking member detachably secures the second block within the first block.

Another embodiment provides a nested chamfer speed block including a first block having a first pair of slots for guiding a saw blade during a femoral cutting operation. A cavity is formed in the first block. Also, a first securing interlock is formed in the first block. A second block is detachably mounted in the cavity and includes a pair of second slots for guiding the saw blade during a chamfer cutting operation. A second securing interlock is provided on the second block. An interlock member engages the first and second securing interlocks for detachably engaging the second block within the first block.

A further embodiment provides a nested chamfer speed block including a first block having a pair of first slots for guiding a saw blade during a first cutting operation. A second block is detachably connected to the first block. The second block includes a pair of second slots for guiding the saw blade during a second cutting operation. The first block includes means for receiving the second block. Means are also provided for detachably interconnecting the first and second blocks. As a result, the first cutting operation is made with the first and second blocks being interconnected and mounted in a cutting position. The second cutting operation is made with the first block detached from the second block and the second block remaining in the cutting position.

A still further embodiment provides a method of making multiple cuts on a distal femur. First, a pair of nested speed blocks are secured on a transverse surface formed on the distal femur. Second, anterior and posterior femoral cuts are made using a first pair of slots formed in a first one of the nested speed blocks. Next, an interlocking member which secures the first one of the nested speed blocks to a second one of the nested speed blocks is removed. Subsequently, the first one of the nested speed blocks is removed from the second one of the nested speed blocks. Next, anterior and posterior chamfer cuts are made on the femur using a pair of second slots formed in the second one of the nested speed blocks. Finally, securing members are removed from the second one of the nested speed blocks and from the distal femur to permit removal of the second one of the nested speed blocks from the transverse surface.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A nested cutting block comprising:
   a first block including at least one first slot for guiding a saw blade during a first bone cutting operation, and having a cavity formed therein;
   a second block detachably mounted in the cavity and including at least one second slot for guiding the saw blade during a second bone cutting operation; and
   an interlocking member for detachably securing the second block within the first block.

2. The nested block as defined in claim 1 further comprising a first securing interlock on the first block.

3. The nested block as defined in claim 2 wherein the first securing interlock includes a locking recess formed in the first block.

4. The nested block as defined in claim 2 further comprising a second securing interlock on the second block.

5. The nested block as defined in claim 4 wherein the second securing interlock includes an attachment member extending from the second block.

6. The nested block as defined in claim 5 wherein the interlocking member includes a handle for receiving the attachment member and for nested engagement with the first block.

7. The nested block as defined in claim 6 wherein the at least one first slot is disposed at a first angle for the femoral cutting operation.

8. The speed block as defined in claim 7 wherein the at least one second slot is disposed at a second angle, different from the first angle, for the chamfer cutting operation.

9. The speed block as defined in claim 1 further comprising an anterior referencing member extending from the first block.

10. A nested cutting block comprising:
   a first block including a first pair of slots for guiding a saw blade during a first bone cutting operation, and having a cavity formed therein;
   a first securing interlock on the first block;
   a second block detachably mounted in the cavity and including a pair of second slots for guiding the saw blade during a second bone cutting operation;
   a second securing Interlock on the second block; and
   an interlock member engaging the first and second securing interlocks for detachably engaging the second block within the first block, wherein the first and second bone cutting operations are femoral and chamfer cutting operations and include an anterior cutting operation and a posterior cutting operation.

11. The nested cutting block as defined in claim 10 wherein the first securing interlock includes a locking recess formed in the first block, the second securing interlock includes an attachment member extending from the second block, and the interlock member includes a handle for receiving the attachment member and for nested engagement with the locking recess.

12. The nested cutting block as defined in claim 11 further comprising means for securing the second block to a bone during the first and second bone cutting operations.

13. The nested cutting block as defined in claim 11 wherein the first and second bone cutting operations are femoral and chamfer cutting operations.

14. The nested block as defined in claim 13 wherein the femoral and chamfer cutting operations include an anterior cutting operation and a posterior cutting operation.

15. The nested cutting block as defined in claim 11 wherein the first slots are disposed at a first angle for the first bone cutting operation.

16. The nested cutting block as defined in claim 15 wherein the second slots are disposed at a second angle, different from the first angle, for the second bone cutting operation.

17. The nested cutting block as defined in claim 11 further comprising an anterior referencing member extending from the first block.

18. A nested cutting block comprising:
   a first block including at least one first slot for guiding a saw blade during a first cutting operation;
   a second block detachably connected to the first block, the second block including at least one second slot for guiding the saw blade during a second cutting operation;
   means on the first block for receiving the second block; and
   means for detachably Interconnecting the first and second blocks, whereby the first cutting operation is made with the first and second blocks being interconnected and mounted in a cutting position, and the second cutting operation is made with the first block detached from the second block and the second block remaining in the cutting position, wherein the first and second bone cutting operations are femoral and chamfer cutting operations and include an anterior cutting operation and a posterior cutting operation.

19. A nested chamfer speed block comprising:
   a first block having a cavity formed therein;
   a first securing interlock on the first block;
   a second block detachably mounted in the cavity of the first block;
   a second securing interlock on the second block;
   a first and a second pair of slots for guiding a saw blade during a femoral and chamfer cutting operation, respectively;
   the first block and the first pair of slots being optionally removable from the second block after the femoral cutting operation is completed, to permit improved visual contact of the second pair of slots and the second block during the chamfer cutting operation; and
   an interlock member engaging the first and second securing interlocks for detachably engaging the second block with the first block, wherein the first and second bone cutting operations are femoral and chamfer cutting operations and include an anterior cutting operation and a posterior cutting operation.

20. A nested cutting block comprising:
   a first block having a cavity formed therein and including at least one cutting guide for guiding a saw blade during a first bone cutting operation;
   a second block detachably mounted in the cavity of the first block and including at least one cutting guide for guiding a saw blade during a second bone cutting operation, and a securing member for fixedly securing the second block to a bone during the first and second cutting operations;
   an interlocking member for detachably securing the first block to the second block so that the first block may be either secured to or detached from the second block during the second cutting operation, wherein the first and second bone cutting operations are femoral and chamfer cutting operations and include an anterior cutting operation and a posterior cutting operation.

* * * * *